United States Patent [19]

Boguslaski et al.

[11] 4,134,792

[45] Jan. 16, 1979

[54] SPECIFIC BINDING ASSAY WITH AN ENZYME MODULATOR AS A LABELING SUBSTANCE

[75] Inventors: Robert C. Boguslaski; Robert J. Carrico, both of Elkhart, Ind.; James E. Christner, Ann Arbor, Mich.

[73] Assignee: Miles Laboratories, Inc., Elkhart, Ind.

[21] Appl. No.: 748,005

[22] Filed: Dec. 6, 1976

[51] Int. Cl.$^2$ .................. G01N 33/00; G01N 31/14
[52] U.S. Cl. ..................... 195/99; 195/103.5 A; 424/12
[58] Field of Search ............ 195/103.5 A, 99; 424/12

[56] References Cited

U.S. PATENT DOCUMENTS

| 3,817,837 | 6/1974 | Rubenstein et al. | 195/103.5 A |
| 3,850,752 | 11/1974 | Schuurs et al. | 195/103.5 A |
| 3,880,934 | 4/1975 | Rammler | 195/103.5 A |
| 3,975,342 | 8/1976 | Gross | 424/12 |
| 4,003,792 | 1/1977 | Mill et al. | 424/12 |

OTHER PUBLICATIONS

Miles et al., Nature, vol. 219, (1968), pp. 186–189.
Landon, "A Suggested Terminology for Non-Isotopic Immunoassays", Conference on Non-isotopic Immunoassays, (1976).

*Primary Examiner*—Alvin E. Tanenholtz
*Assistant Examiner*—C. A. Fan
*Attorney, Agent, or Firm*—Andrew L. Klawitter

[57] ABSTRACT

A specific binding assay method employing, as a labeling substance, a reversibly binding enzyme modulator for the detection of a ligand in a liquid medium. The method follows conventional specific binding assay techniques of either the homogeneous or heterogeneous type wherein the liquid medium to be assayed is combined with reagent means that includes a labeled conjugate to form a binding reaction system having a bound-species and a free-species of the conjugate. The amount of conjugate resulting in the bound-species or the free-species is a function of the amount of ligand present in the liquid medium assayed. In the present invention, the labeled conjugate comprises a reversibly binding enzyme modulator covalently linked to a binding component of the binding reaction system. The distribution of the conjugate between the bound-species and the free-species is determined by addition of an enzyme whose activity is affected, either decreased or increased, by said modulator and measuring the resulting activity of the enzyme. The enzyme modulator may be a conventional enzyme inhibitor, preferably of the coompetitive type, or an allosteric effector.

19 Claims, 2 Drawing Figures

SPECIFIC BINDING ASSAY WITH AN ENZYME MODULATOR AS A LABELING SUBSTANCE

BACKGROUND OF THE INVENTION

1. Field of the Invention

This invention relates to assay methods of the homogeneous and heterogeneous specific binding type for determining qualitatively or quantitatively a ligand in a liquid medium. In a preferred embodiment, the present invention relates to competitive binding immunoassays employing nonisotopic labels.

2. Description of the Prior Art

In conventional specific binding assay techniques, the test sample is combined with reagent means of various compositions that include a conjugate of a labeling substance linked to a binding component which participates with other constituents, if any, of the reagent means to form a binding reaction system producing two species of the labeled conjugate, a bound-species and a free-species. The relative amounts of the labeled conjugate that result in the bound-species and the free-species are a function of the presence or amount of the ligand to be detected in the test sample.

As an illustration, a conventional competitive binding assay technique will now be described. In such a technique the reagent means would comprise (1) a labeled conjugate in the form of the ligand to be detected, or of an appropriate analog thereof, chemically linked to a labeling substance and (2) a specific binding partner for the ligand, such as an antibody or other binding protein. Upon combination of the test sample and the reagent means, the ligand to be detected and the labeled conjugate would compete in a substantially nondiscriminating manner for noncovalent binding to the specific binding partner. As a result, the amount of labeled conjugate that would become bound to the binding partner, i.e., in the bound-species, or that would remain free, i.e., unbound to the binding partner, and, thus, in the free-species, is a function of the amount of competing ligand present.

Where the labeled conjugate in the bound-species and that in the free-species are essentially indistinguishable by the means used to measure the labeling substance, the bound-species and the free-species must be physically separated in order to complete the assay. This type of assay is referred to as "heterogeneous." Where the bound-species and free-species forms of the labeled conjugate can be distinguished, a "homogeneous" format may be followed and the separation step avoided.

The first discovered type of specific binding assay was the radioimmunoassay which employs a radioactive isotope as the labeling substance. Such an assay necessarily must follow the heterogeneous format. Because of the hazard and difficulty of handling radioactive materials, many new assay systems have been devised using materials other than isotopes as the labeling substance, including enzymes, fluoroscent molecules, bacteriophages, coenzymes, and luminescent molecules.

The following describe several different heterogeneous binding reaction systems in which an enzyme is employed as the labeling substance: U.S. Pat. Nos. 3,654,909; 3,791,932; 3,839,153; 3,850,752; and 3,879,262; *J. Immunol. Methods* 1:247 (1972); and *J. Immunol.* 109:129(1972). A heterogeneous binding assay utilizing a non-active precursor of a spectrophotometrically detectable substance as the labeling substance is suggested in U.S. Pat. No. 3,880,934. Of further background interest pertaining to heterogeneous assays is *Principles of Competitive Protein-Binding Assays*, ed. Odell and Daughaday (J. B. Lippincott Co., Philadelphia, 1972). An enzyme-labeled immunoassay of the homogeneous type is described in U.S. Pat. No. 3,817,834 wherein a ligand-enzyme conjugate is employed. The enzymatic activity of the conjugate in the bound-species is measurably less than that in the free-species, thereby allowing a homogeneous format to be used. The use of particularly unique materials as labeling substances, including coenzymes, luminescent molecules, and cleavable fluorescent substrates, in both homogeneous and heterogeneous formats, is described in U.S. patent applications Ser. Nos. 667,982 and 667,996, filed on Mar. 18, 1976, and assigned to the instant assignee.

It is a primary object of the present invention to provide a specific binding assay method, useable in both the homogeneous and heterogeneous modes, which employs a unique labeling substance belonging to a large class of compounds for which there is an extensive literature background to facilitate selection of specific labels, approaches to derivatization, and monitoring reactions.

SUMMARY OF THE INVENTION

The present invention provides a specific binding assay method employing, as a labeling substance, a reversibly binding enzyme modulator. The inventive labeling substance may be used in both homogeneous and heterogeneous binding assay formats wherein the liquid medium to be assayed for a ligand is combined with reagent means which includes a labeled conjugate to form a binding reaction system having a bound-species and a free-species of the conjugate. The amount of conjugate resulting in the bound-species or the free-species is a function of the presence or amount of ligand present in the liquid medium assayed. In the present invention, the labeled conjugate comprises a reversibly binding enzyme modulator covalently linked to a binding component of the binding reaction system. The distribution of the conjugate between the bound-species and the free-species is determined by addition of an enzyme whose activity is affected, either in an inhibitory or stimulatory manner, by said modulator and measuring the resulting activity of the enzyme following the desired homogeneous or heterogeneous assay scheme.

DESCRIPTION OF THE PREFERRED EMBODIMENTS

Figure 1:
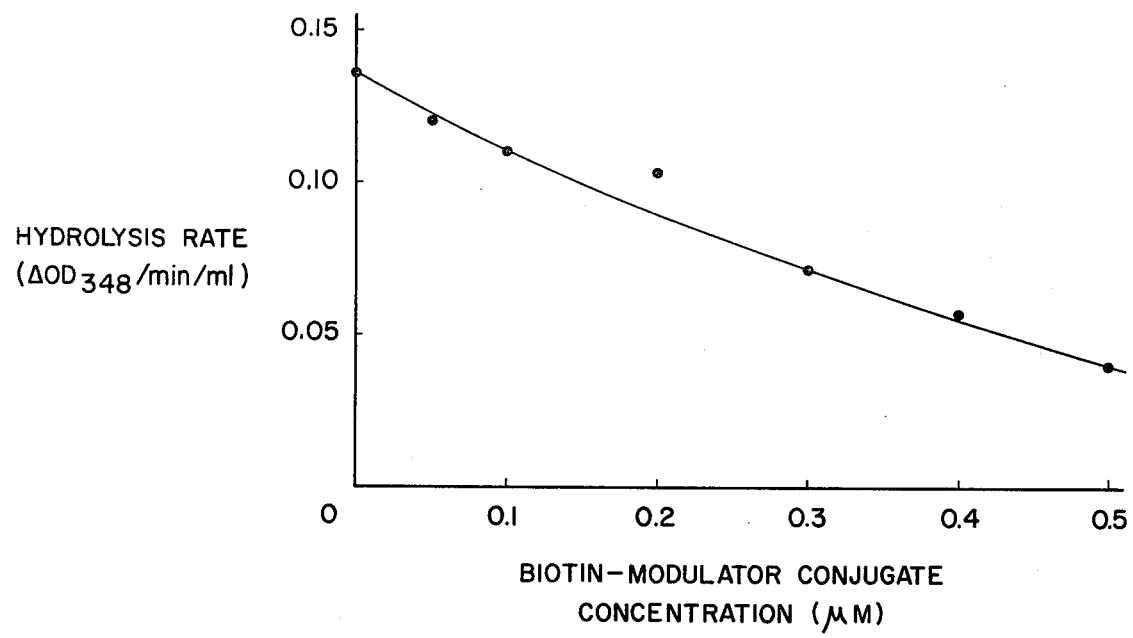
FIG. 1 is a graphic representation of the inhibitory effect of various concentrations of biotin-modulator conjugate on the esterase activity of carbonic anhydrase measured by hydrolysis rate.

In the context of this disclosure, the following terms shall be defined as follows: "ligand" is the substance, or group of substances, whose presence or the amount thereof in a liquid medium is to be determined; "specific binding partner of the ligand" is any substance, or group of substances, which has a specific binding affinity for the ligand to the exclusion of other substances; "specific binding analog of the ligand" is any substance, or group of substances, which behaves essentially the same as the ligand with respect to the binding affinity of the specific binding partner for the ligand; and "monitoring reaction" is a reaction catalyzed by an enzyme whose activity is affected (i.e., decreased or increased) by the enzyme modulator of the present invention.

The novel labeling substance of the present invention is any chemical substance which binds specifically or nonspecifically with an enzyme in a reversible, noncovalent manner and thereby measurably affects, either in an inhibitory or stimulatory manner, the catalytic activity of the enzyme relative to a predetermined reaction, i.e., the monitoring reaction for the binding reaction system formed in the present assay method. By "reversibly binding" is meant that the binding constant for the association of the enzyme modulator and the enzyme that catalyzes the monitoring reaction is less than about $10^{11}$ molar$^{-1}$. Preferably, the binding constant is between about $10^5$ and about $10^9$ molar$^{-1}$.

One class of substances which encompasses usable enzyme modulators is the group of reversibly binding enzyme inhibitors, whether of the competitive, uncompetitive, or noncompetitive type. Competitive inhibitors combine with the free enzyme in such a way that they compete with the normal substrate for binding at the active site of the enzyme, however, the inhibitor molecule is not chemically transformed by the enzyme. In contrast, uncompetitive inhibitors do not combine with the free enzyme or affect its association with the normal substrate; rather, they combine with the formed enzyme-substrate complex to yield an inactive adduct that is incapable of releasing the normal product. Noncompetitive inhibitors, on the other hand, can combine with either the free enzyme or the enzyme-substrate complex to interfere with normal catalysis, usually by binding at a site on the enzyme other than the active site to alter the sensitive configuration of the active enzyme.

Of the conventional enzyme inhibitors, those of the competitive type are preferred. Following is a table of some useful competitive inhibitors, the enzymes whose activity is inhibited thereby, and an approximation of the inhibitor constants ($K_i$) for the dissociation of the respective inhibitors from the enzymes.

| Inhibitor | Enzyme | ($K_i$(molar) |
|---|---|---|
| acetazolamine | carbonic anhydrase | $6 \times 10^{-7}$ |
| sulfanilamide | carbonic anhydrase | $10^{-9}$ |
| phenyl trimethyl-ammonium ion | acetylcholinesterase | $10^{-6}$ |
| saccharo-1,4-lactone | β-glucuronidase | $10^{-6}$ |
| 4-amino-10-methyl-pteroylglutamic acid | dihydrofolate reductase | $10^{-9}$ |
| 2,6,8-trichloro-purine | uricase | $10^{-6}$ |

Effective analogs, i.e., derivatives, homologs, and so forth, of the above-listed inhibitors can also be used. For example, acetylcholinesterase is also inhibited by p-aminophenyl trimethylammonium ion and also by the N-methyl-N-(p-aminophenyl) carbamate ester of m-(trimethylamino) phenol.

Another class of substances from which a useful enzyme modulator can be selected is that of allosteric effectors. Such substances act in biological processes as regulators of enzymatic metabolism. Their action is accomplished by binding specifically to a site on the regulated enzyme other than the substrate active site and thereby to inhibit or stimulate, such as by a conformational change, the activity of the enzyme. Following is a table of some allosteric effectors contemplated to be useful as the enzyme modulator of the present invention. In the table, inhibitory or negative effectors are indicated by (−) and stimulatory or positive effectors are indicated by (+). The source of the affected enzyme is also given in parentheses.

| Allosteric Effector | Enzyme |
|---|---|
| L-isoleucine (−) | biosynthetic L-threonine deaminase |
| L-valine (+) | (E. coli K12) and (yeast) |
| cytosine triphosphate (CTP) (−) | aspartate transcarbamylase (E. coli) |
| adenosine triphosphate (ATP) (+) | |
| deoxythymidine triphosphate (dTTP) (−) | deoxycytidylate aminohydrolase (ass spleen) |
| deoxycytosine triphosphate (dCTP) (+) | |
| ATP(−) | phosphofructokinase (guinea pig heart) |
| 3',5'-adenosine monophosphate (AMP) (+) | |
| dTTP(−) | deoxythymidine kinase (E. coli) |
| deoxycytosine diphosphate dCDP(+) | |
| α-ketoglutarate(−) | nicotinamide adenine dinucleotide (NAD)-isocitric dehydrogenase (N. crassa) |
| citrate (+) | |
| 5'-AMP(+) | NAD-isocitric dehydrogenase (yeast) |
| L-threonine(−) | homoserine dehydrogenase (R. rubrum) |
| L-isoleucine(+) | |
| L-methionine(+) | |
| adenosine diphosphate (ADP) (+) | L-threonine deaminase (C. tetanomorphum) |
| L-valine(+) | acetolactate synthetase (E. coli) |
| L-threonine(−) | threonine aspartokinase (E. coli) |
| uridine diphosphate (UDP)-N-acetyl-glucosamine(−) | L-glutamine-D-fructose-6-phosphate transaminase (rat liver) |
| glucose-6-phosphate(+) | glycogen synthetase (yeast) and (lamb muscle) |
| ATP(−) | glutamate dehydrogenase (beef liver) |
| guanosine triphosphate (GTP) (−) | |
| reduced NAD(−) | |
| estrogens(−) | |
| thyroxine(−) | |
| ADP(+) | |
| leucine(+) | |
| methionine(+) | |
| ATP(−) | phosphorylase b (rabbit muscle) |
| 5'-AMP(+) | |
| cytosine monophosphate (CMP)-N-acetyl-neuraminic acid(−) | UDP-N-acetyl-glucosamine-2-epimerase (rat liver) |
| L-threonine(−) | homoserine dehydrogenase (E. coli) |
| L-lysine(−) | lysine aspartokinase (E. coli) |
| 5'-AMP(−) | fructose-1,6-diphosphatase (frog muscle) and (rat liver) |

Further details may be found in *J. Mol. Biol.* 12:88(1965).

To form the labeled conjugate which participates in the binding reaction system, the enzyme modulator is covalently linked to an appropriate binding component of such reaction system. Such binding component is the ligand to be detected, a specific binding analog of the ligand, or a specific binding partner of the ligand, depending upon the binding reaction scheme selected. Some of the various available binding reaction schemes will be described in detail hereinafter. The method used to covalently link the enzyme modulator and the binding component is not critical so long as the resulting enzyme modulator moiety retains a measurable amount of modulating activity and, similarly, the resulting binding component moiety retains a useful amount of activity with respect to the binding reaction system. In general, the enzyme modulator and the binding component are linked directly or by a chain bridge group having active coupling groups at opposite ends to covalently bind to the respective moieties to be linked. The bridge group usually comprises between 1 and 50, and preferably between 1 and 10, carbon atoms or heteroatoms such as nitrogen, oxygen, sulfur, phosphorus, and so forth. Examples of a bridge group comprising a single atom would be a methylene group (one carbon atom in the chain) and an amino group (one heteroatom in the chain). The bridge group usually has a molecular weight not exceeding 1000 and preferably less than 200. The bridge group, if present, comprises a chain of carbon atoms and/or heteroatoms and is joined to the enzyme modulator and the binding component, respectively, by connecting groups, usually selected from ester, amide, ether, thioester, acetal, methylene, and amino groups.

Following are structural formulae of contemplated labeled conjugates including the competitive inhibitors previously listed as the labeling substance and a general method for their preparation.

A. Acetazolamide - binding component conjugates

Example 1, Parts B and C provide details of preparations of these types of conjugates.

B. Phenyl trimethylammonium ion - binding component conjugates

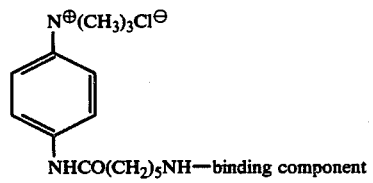

The binding component of interest is covalently linked to the amino function of an o-aminoalkyl carboxylic acid through a reaction such as nucleophilic displacement. The resulting product is then coupled to p-amino-N,N-dimethylaniline via an activating agent, such as carbodiimide. The resulting product is then treated with methyl iodide to give the desired conjugate.

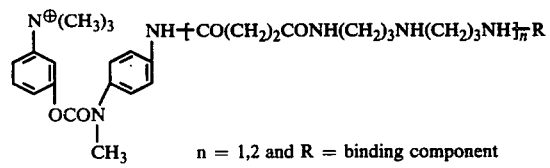

n = 1,2 and R = binding component

The binding component of interest is coupled through any appropriate means (activation of the carboxyl group, nucleophilic displacement) to one amino group of 3,3'-diaminodipropylamine. The resulting product is then treated with succinic anhydride. The resulting material is then coupled to the free amino function of the N-methyl-N-(p-aminophenyl) carbamate ester of m-(triethylamino)-phenol via a carboxylic acid activating agent. Alternatively, the inhibitor could be extended further from the ligand by treatment of the above succinylated derivative with 3,3'-diaminodipropylamine and carbodiimide, followed by succinic anhydride and coupling to the inhibitor (n=2).

C. Saccharo-1,4-lactone - binding component conjugate

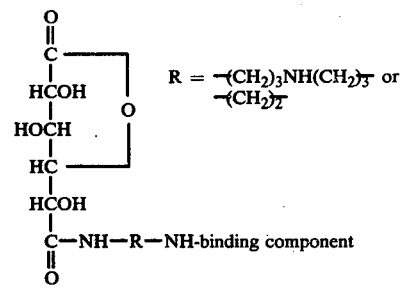

Saccharo-1,4-lactone is coupled to an α,ω-diaminoalkyl derivative through its free carboxyl group using a carboxylic acid activating agent. The resulting product is then coupled to the binding component of interest using any appropriate reaction, e.g., nucleophilic displacement, carboxylic acid activation, etc.

D. 4-Amino-10-methylpteroylglutamic acid - binding component conjugate

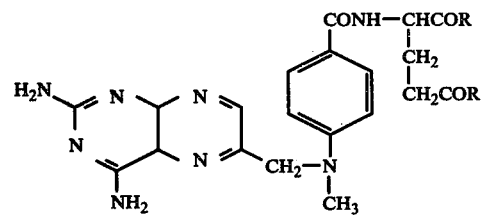

R = —OH or —NH(CH$_2$)$_n$-binding component
n = 6 or 12

The binding component of interest is coupled to amino function of an α,ω-diaminoalkyl derivative through an appropriate reaction sequence. The product from this reaction is then coupled to one of the carboxylic acid functions of 4-amino-10-methyl pteroyl glutamic acid via an appropriate carboxylic acid activating agent, e.g., carbodiimide.

E. 2,6,8-Trichloropurine - binding component conjugate

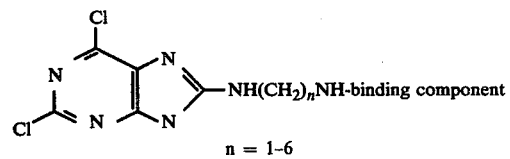

n = 1-6

2,6,8-Trichloropurine is treated with dihydropyran and a catalytic amount of acid to produce a 9-substituted tetrahydropyranyl ether. This product is then reacted with an α,ω-diaminoalkane to produce a C-8 substituted aminoalkylamine derivative. The tetrahydropyranyl blocking group is then removed under acidic conditions to give a 2,6-dichloro-substituted purine. The binding component of interest is then coupled to the free alkyl amino group through any appropriate reaction sequence.

The present assay method may be applied to the detection of any ligand for which there is a specific binding partner. The ligand usually is a peptide, protein, carbohydrate, glycoprotein, steroid, or other organic molecule for which a specific binding partner exists in biological systems or can be synthesized. The ligand, in functional terms, is usually selected from the group consisting of antigens and antibodies thereto; haptens and antibodies thereto; and hormones, vitamins, metabolites and pharmacological agents, and their receptors and binding substances. Specific examples of ligands which may be detected using the present invention are hormones such as insulin, chorionic gonadotropin, thyroxine, liothyronine, and estriol; antigens and haptens such as ferritin, bradykinin, prostaglandins, and tumor specific antigens; vitamins such as biotin, vitamin $B_{12}$, folic acid, vitamin E, and ascorbic acid; metabolites such as 3',5' adenosine monophosphate and 3',5' guanosine monophosphate; pharmacological agents such as dilantin, digoxin, morphine, digitoxin, and barbiturates; antibodies such as microsomal antibody and antibodies to hepatitis and allergens; and specific binding receptors such as thyroxine binding globulin, avidin, intrinsic factor, and transcobalamin.

As stated previously, the present assay method may follow, in appropriate circumstances, either a homogeneous or a heterogeneous scheme.

HOMOGENEOUS SCHEMES

A homogeneous scheme, i.e., one which does not require a physical separation of the bound-species and the free-species, is available where reaction between the binding component of the labeled conjugate and a corresponding binding partner causes a measurable change, either in a positive or a negative sense, in the ability of the conjugated enzyme modulator to affect the activity of the enzyme that catalyzes the monitoring reaction. In such a case, the distribution of the enzyme modulator between the bound-species and the free-species can be determined by adding the enzyme directly to the combined species and measuring therein the activity of the enzyme. Several manipulative schemes are available for carrying out a homogeneous assay with the preferred being the direct binding and the competitive binding techniques.

In the direct binding technique, a liquid medium suspected of containing the ligand to be detected is contacted with a conjugate comprising the enzyme modulator coupled to a specific binding partner of the ligand, and any change in the activity of the enzyme modulator is assessed. In the competitive binding technique, the liquid medium is contacted with a specific binding partner of the ligand and with a conjugate comprising the enzyme modulator coupled to one or both of the ligand or a specific binding analog thereof, and thereafter any change in the activity of the enzyme modulator is assessed. In both techniques, the activity of the enzyme modulator is determined by contacting the liquid medium with at least one reagent which forms, with the enzyme modulator, the predetermined monitoring reaction. Qualitative determination of the ligand in the liquid medium involves comparing a characteristic, usually the rate, of the resulting reaction to that of the monitoring reaction in a liquid medium devoid of the ligand, any difference therebetween being an indication of a change in activity of the enzyme modulator. Quantitative determination of the ligand in the liquid medium involves comparing a characteristic of the resulting reaction to that of the monitoring reaction in liquid media containing known amounts of the ligand.

In general, when following the homogeneous assay scheme, the components of the specific binding reaction, i.e., the liquid medium suspected of containing the ligand, the conjugate, and/or a specific binding partner of the ligand, may be combined in any amount, manner, and sequence, provided that the activity of the enzyme modulator in the conjugate is measurably altered when the liquid medium contains the ligand in an amount or concentration of significance to the purposes of the assay. Preferably, all of the components of the specific binding reaction are soluble in the liquid medium.

Where a direct binding homogeneous technique is used, the components of the binding reaction are the liquid medium suspected of containing the ligand and a quantity of a conjugate comprising the enzyme modulator coupled to a specific binding partner of the ligand. The activity of the conjugated modulator on contact with the liquid medium varies inversely with the extent of binding between the ligand in the liquid medium and the specific binding partner in the conjugate. Thus, as the amount of ligand in the liquid medium increases, the activity of the conjugated modulator decreases.

Where a competitive binding homogeneous technique is used, the components of the binding reaction are the liquid medium suspected of containing the ligand, a quantity of a conjugate comprising the enzyme modulator coupled to the ligand or a specific binding analog of the ligand, and a quantity of a specific binding partner of the ligand. The specific binding partner is contacted substantially simultaneously with both the conjugate and the liquid medium. Since any ligand in the liquid medium competes with the ligand or specific binding analog thereof in the conjugate for binding with the specific binding partner, the activity of the conjugated modulator on contact with the liquid medium varies directly with the extent of binding between the ligand in the liquid medium and the specific binding partner. Thus, as the amount of the ligand in the liquid medium increases, the activity of the conjugated modulator increases.

A variation of the competitive binding homogeneous technique is the displacment binding homogeneous technique wherein the conjugate is contacted first with the specific binding partner of the ligand and thereafter with the liquid medium. Competition for the specific binding partner then occurs. In such a method, the amount of the conjugate contacted with the specific binding partner is usually that which comprises the ligand or analog thereof in excess of that capable of binding with the amount of the specific binding partner present during the time that the conjugate and the specific binding partner are in contact prior to contact with the liquid medium suspected of containing the ligand. This order of contact may be accomplished in either of two convenient ways. In one method, the conjugate is contacted with the specific binding partner in a liquid environment prior to contact with the liquid medium suspected of containing the ligand. In the second method, the liquid medium suspected of containing the ligand is contacted with a complex comprising the conjugate and the specific binding partner, the specific binding substance in the conjugate and the specific binding partner being reversibly bound to each other. The amount of the conjugate that becomes bound to the specific binding partner in the first method or which is in complexed form in the second method is usually in excess of that capable of being displaced by all of the ligand in the liquid medium in the time that the specific binding partner, or complex, and the medium are in contact prior to the completion of the assessment of any change in the activity of the conjugated modulator.

Another variation of the competitive binding homogeneous technique is the sequential saturation homogeneous technique wherein the components of the specific binding reaction are the same as those used in the competitive binding technique, but the order of addition or combination of the components and the relative amounts thereof used are different. Following a sequential saturation technique, the specific binding partner of the ligand is contacted with the liquid medium suspected of containing the ligand for a period of time prior to the contact of said liquid medium with the conjugate. The amount of the specific binding partner contacted with the liquid medium is usually in excess of that capable of binding with all of the ligand thought to be present in the liquid medium in the time that the specific binding partner and the liquid medium are in contact prior to the time that the liquid medium is contacted with the conjugate. Further, the amount of the ligand or ligand analog in conjugated form is usually in excess of that capable of binding with the remaining unbound amount of the specific binding partner during the time that the liquid medium and the conjugate are in contact prior to the completion of the assessment of any change in activity of the conjugated modulator.

HETEROGENEOUS SCHEMES

The use of an enzyme modulator as labeling substance can also be applied to the conventional heterogeneous type assay schemes wherein the bound- and free-species of the labeled constituent are separated and the quantity of labeling substance in one and/or the other is determined. The reagent means for performing such a heterogeneous assay may take on many different forms. In general, such means comprises three basic constituents, which are (1) the ligand to be detected, (2) a specific binding partner of the ligand, and (3) a labeled constituent which is normally a labeled form of (a) the ligand, (b) a specific binding analog of the ligand, or (c) the specific binding partner. The binding reaction constituents are combined simultaneously or in a series of additions, and with an appropriate incubation period or periods, the labeled constituent becomes bound to its corresponding competing binding partners such that the extent of binding, i.e., the ratio of the amount of labeled constituent bound to a binding partner to that unbound, is a function of the amount of ligand present. To follow is a brief description of some of the different heterogeneous binding reaction schemes that may be used in carrying out the method of the present invention.

For the diagrams which are set out hereinafter, the following legend shall apply:

| Symbol | Definition |
|---|---|
| L | ligand to be detected in sample |
| (L) | ligand or specific binding analog thereof |
| B | binding partner for the ligand |
| * | labeling substance, i.e., enzyme modulator |
| ├ | insoluble phase |
| ⟶ | incubation period |
| (sep) | appropriate separation of the |

| Symbol | Definition |
|---|---|
| (lim) | bound- and free-species limited; present in an amount less than that capable of being bound to the total available binding sites under the selected reaction conditions during the selected incubation period; i.e., the constituent for which the other constituents compete for binding |
| (exc) | excess; present in an amount greater than that capable of being bound by the total available binding sites under the selected reaction conditions during the selected incubation period |

1. Competitive binding heterogeneous formats

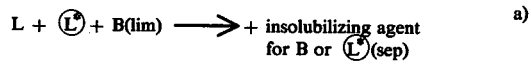
a)

This is the classical competitive binding approach. Examples of insolubilizing agents are specific precipitating antibodies, specific insolubilized antibodies, and, where B or (L)* is a proteinaceous material, protein precipitators such as ammonium sulfate, or where B or (L)* is a small adsorbable molecule, dextran-coated charcoal. Description of parallel systems may be found in *Biochem. J.* 88:137 (1963) and U.S. Pat. No. 3,839,153.

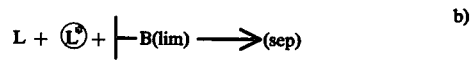
b)

This approach is commonly referred to as the solid-phase technique. Descriptions of parallel radioimmunoassay and enzyme immunoassay techniques may be found in U.S. Pat. Nos. 3,505,019; 3,555,143; 3,646,346; and 3,654,090.

c)

Reference: U.S. Pat. No. 3,654,090.

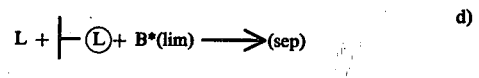
d)

Reference: U.S. Pat. No. 3,850,752.

2. Sequential saturation heterogeneous formats

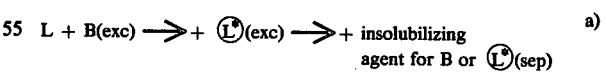
a)

In the sequential saturation technique, some or all the binding sites on B remaining after the first incubation period are bound by the labeled constituent.

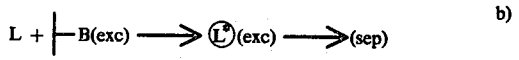
b)

Descriptions of parallel radioimmunoassay and enzyme immunoassay techniques may be found in U.S. Pat. No. 3,720,760 and *J. Immunol.* 209:129(1972).

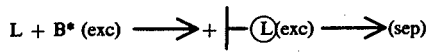

3. "Sandwich" heterogeneous format

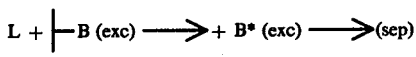

In the sandwich technique, some or all of the ligand molecules bound to the insolubilized binding partners are bound by the labeled constituent.
Reference: U.S. Pat. No. 3,720,760.

4. Solid-phase ligand adsorbent format

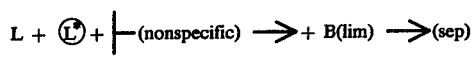

In this technique, the ligand and the labeled constituent are bound to a non-specific binder and thereafter proportional amounts are dissociated therefrom by binding with a binding partner having a greater affinity than the binder for the ligand and the labeled constituent. The most useful form of this technique employs a column of the non-specific binder as described in U.S. Pat. No. 3,659,104. Such a technique is useful where the ligand is bound to endogenous binding substances in the sample which unless removed would interfer with the competitive binding reaction. Upon being bound to the non-specific binder, the endogenous binding substances may be removed by appropriate washes.

For further discussion of the parameters involved in conventional heterogeneous assay systems, such as more detailed descriptions of assay formats and alternative separation techniques, reference may be had to *Principles of Competitive Protein-Binding Assays*, ed. Odell and Daughaday (J. B. Lippincott Co., Philadelphia, 1972).

It is contemplated that manipulative schemes involving other orders of addition and other binding reaction formats may be devised for carrying out homogeneous and heterogeneous specific binding assays without departing from the inventive concept embodied herein.

The liquid medium to be tested may be a naturally occurring or artificially formed liquid suspected of containing the ligand, and usually is a biological fluid or a liquid resulting from a dilution or other treatment thereof. Biological fluids which may be assayed following the present method include serum, plasma, urine, and amniotic, cerebral, and spinal fluids. Other materials such as solid matter, for example tissue, or gases may be assayed by reducing them to a liquid form such as by dissolution of the solid or gas in a liquid or by liquid extraction of the solid.

The present invention will now be illustrated, but is not intended to be limited, by the following examples.

EXAMPLE 1

Preparation of Materials

A. Carbonic anhydrase

The enzyme was isolated from human red blood cells by the procedure of Armstrong et al, *J. Biol. Chem.* 241:5137–5149 (1966), except that the dialysis was omitted prior to the precipitation with ammonium sulfate. The precipitate was dissolved in 0.05 M tris-(hydroxymethyl)-aminomethane hydrochloride (Tris-HCl) buffer, pH 8.7, and chromatographed on a 2.5×55 cm column of DEAE-cellulose equilibrated with the same buffer. The enzyme was eluted as one peak with the Tris-HCl buffer.

B. 5-(Cis-hexahydro-2-oxo-1H-thieno[3,4-d]imidazole)-N-(5-sulfonamido-1,3,4-thiadiazo-2-yl)valeramide

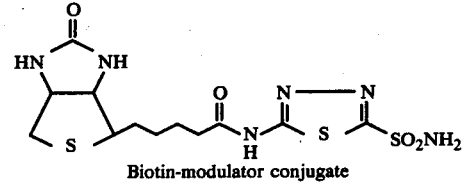
Biotin-modulator conjugate

A solution of anhydrous biotin (300 mg; 1.2 mmol) in dry dimethyl formamide (19.5 ml) was stirred at −10° C. under dry nitrogen and dry triethylamine (0.17 ml; 1.2 mmol) was added [Knappe et al, *Biochem Z.* 338:559(1963)]. A solution of freshly distilled ethyl chloroformate (0.141 ml in 3 ml of dry diethylether) was added dropwise and a white precipitate formed. The mixture as stirred at −10° C. for 30 min and then filtered under an atmosphere of dry nitrogen. The filtrate was cooled immediately to −10° C. and a solution of 2-amino-1,3,4-thiadiazole-5-sulfonamide (438 mg; 2.43 mmol) [Roblin et al, *J. Am. Chem. Soc.* 72:4890–4892(1950)] in 3 ml of dry pyridine was added. The resulting solution was stirred at −10° C. for 15 min and then at room temperature for 30 min. The solvents were evaporated under vacuum at 40° C., leaving an oily residue. The oil was stirred ast 0° C. with 50 ml 0.3 N hydrochloric acid. The resulting white solid (400 mg) was collected by filtration and dissolved in 10% (by weight) sodium bicarbonate. This solution was cooled in an ice bath and adjusted to pH 6.5 with concentrated hydrochloric acid. The resulting beige precipitate was collected by filtration, giving 130 mg (m.p. 254° C. with decomposition). Crystallization from methanol gave 60 mg of a white product (m.p. 262°–263° C. with decomposition).

Analysis calculated for $C_{12}H_{18}N_6O_4S_3$:C, 35.46; H, 4.46; N, 20.67. Found: C, 35.62; H, 4.47; N, 20.55.

C. 6-(2,4-Dinitroanilino)-N-(5-sulfonamide-1,3,4-thiadiazo-2-yl) caproamide

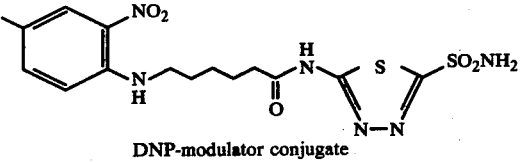
DNP-modulator conjugate

A solution of anhydrous 6-(2,4-dinitroanilino) caproic acid (357 mg; 1.2 mmol), [Garkusha et al, *Obshchei Khim* 29: 1554–1558(1959)] was converted to the mixed anhydride following the stepwise addition of triethylamine and ethylchloroformate as described in Part B above. The filtrate was cooled immediately to −10° C. and the product was mixed at −10° C. with a solution of 2-amino-1,3,4-thiadiazole-5-sulfonamide (438 mg; 2.43 mmol) (obtained in the same manner as described in part B above) in 3 ml of dry pyridine. The reaction was stirred at 0° C. for 20 hrs and then the solvents were evaporated at 30° C. under vacuum. The residue was stirred for 1 hr at 0° C. with 100 ml 1.5 N hydrochloric acid and the resulting yellow precipitate was collected by filtration and stirred for 1 hr at 0° C. with 100 ml 10% (by weight) sodium hydroxide. The yellow solid was collected by filtration and recrystallized from aqueous methanol to give 50 mg of yellow solid (9% yield, m.p. 229°–233° C.).

Analysis calculated for $C_{14}H_{17}N_7O_7S_2$: C, 36.60; H. 3.73; N, 21.34. Found: C, 37.07; H, 3.96; N, 21.19.

D. Reagent Solutions (1) Acetazolamide Reagent - 2-Acetylamino-1,3,4-thiadiazole-5-sulfonamide (1.6 mg) was dissolved in several drops of dimethylsulfoxide and diluted to 50 ml with water. Further dilutions were with water.

(2) Biotin- and DNP-Modulator Reagents - The biotin-modulator conjugate (2.0 mg) and the DNP-modulator conjugate (1.7 mg) were each dissolved in 10 ml 0.1 M sodium carbonate buffer, pH 10.5. Further dilutions were with water.

(3) Avidin Reagent - Lyophilized avidin (Sigma Chemical Co., St. Louis, Mo.) was dissolved in 10 mM Tris-HCl buffer, pH 7.4, at a level of 10.5 activity units per ml (one unit = amount capable of binding 1 $\mu$g of biotin).

(4) Antibody to Dinitrophenyl (DNP) Reagent - Antisera raised against DNP was chromatographed at 4° C. on a 5 × 70 cm column of Sephadex G-200 (Pharmacia AB, Uppsala, Sweden) with 0.1 M Tris-HCl buffer, pH 8.2, containing 1 M sodium chloride. The second eluted peak determined by optical density monitored at 280 nm contained the antibody activity to DNP.

(5) p-Nitrophenyl Acetate Reagent - 5 mg in 0.3 ml acetone adjusted to 10 ml with distilled water with stirring.

EXAMPLE 2

Esterase Activities of Carbonic Anhydrase as a Function of Acetazolamide Concentration Carbonic anhydrase, 0.013 International Units, was incubated for 5 min at room temperature in a series of 0.66 ml aqueous solutions containing, respectively, 100 $\mu$l 0.1 M diethylmalonic buffer, pH 7.4, and the concentrations of acetazolamide and avidin given in Table 1 (concentrations of acetazolamide and avidin based on 1 ml final volume). p-Nitrophenyl Acetate Reagent (0.33 ml) was added to each solution to give a total volume of 1 ml. The hydrolysis rate for p-nitrophenyl acetate was determined by monitoring absorbance at 348 nm.

The results, expressed as the average of duplicate measurements, are presented in Table 1.

Table 1

| Acetazolamide Concentration ($\mu$M) | Avidin (units/ml) | Hydrolysis Rate ($\Delta OD_{348}$/min/ml) |
|---|---|---|
| 0.000 | — | 0.136 |
| 0.144 | — | 0.088 |
| 0.288 | — | 0.047 |
| 0.144 | 0.105 | 0.089 |
| 0.000 | — | 0.111 |
| 0.000 | 0.105 | 0.106 |

These data indicate that acetazolamide inhibited the enzyme carbonic anhydrase and that the presence of avidin had no significant effect on such inhibition.

EXAMPLE 3

Esterase Activities of Carbonic Anhydrase as a Function of Biotin-Modulator Conjugate Concentration Carbonic anhydrase, 0.027 International Units, was incubated for 5 min at room temperature in a series of 0.66 ml aqueous solutions containing 100 $\mu$l 0.1M diethylmalonic buffer, pH 7.4, and the concentrations of the biotin-modulator conjugate (prepared according to Example 1, Part B) indicated in Table 2 (concentration of conjugate based on 1 ml final volume). Esterase activity, as measured by hydrolysis rate, was determined for each reaction mixture as in Example 2. The results are presented in Table 2 and in graphical form in FIG. 1 of the drawing.

Table 2

| Biotin-Modulator Conjugate Concentration ($\mu$M) | Hydrolysis Rate ($\Delta OD_{348}$/min/ml) |
|---|---|
| 0.00 | 0.136 |
| 0.05 | 0.120 |
| 0.10 | 0.109 |
| 0.20 | 0.103 |
| 0.30 | 0.071 |
| 0.40 | 0.057 |
| 0.50 | 0.040 |

These data indicate that the biotin-modulator conjugate possesses useful inhibitory properties relative to carbonic anhydrase and is slightly less efficient than the underivatized inhibitor, acetazolamide.

EXAMPLE 4

Direct Binding Assay for Avidin; Competitive Binding Assay for Biotin; Use of Derivatized Acetazolamide as Labeling Substance A series of binding reaction mixtures were prepared, each to a volume of 0.66 ml and containing 100 $\mu$l 0.1M diethylmalonic buffer, pH 7.4, and the concentrations of biotin-modulator conjugate (prepared as in Example 1, Part B), biotin, and avidin indicated in Table 3 (indicated concentrations based on 1 ml final volume). After a 5 min incubation at room temperature, 0.027 International Units carbonic anhydrase was added to each reaction mixture followed by an additional 5 min incubation. p-Nitrophenyl Acetate Reagent (0.33 ml) was then added to each and the rate of hydrolysis measured by monitoring absorbance at 348 nm.

Figure 2:
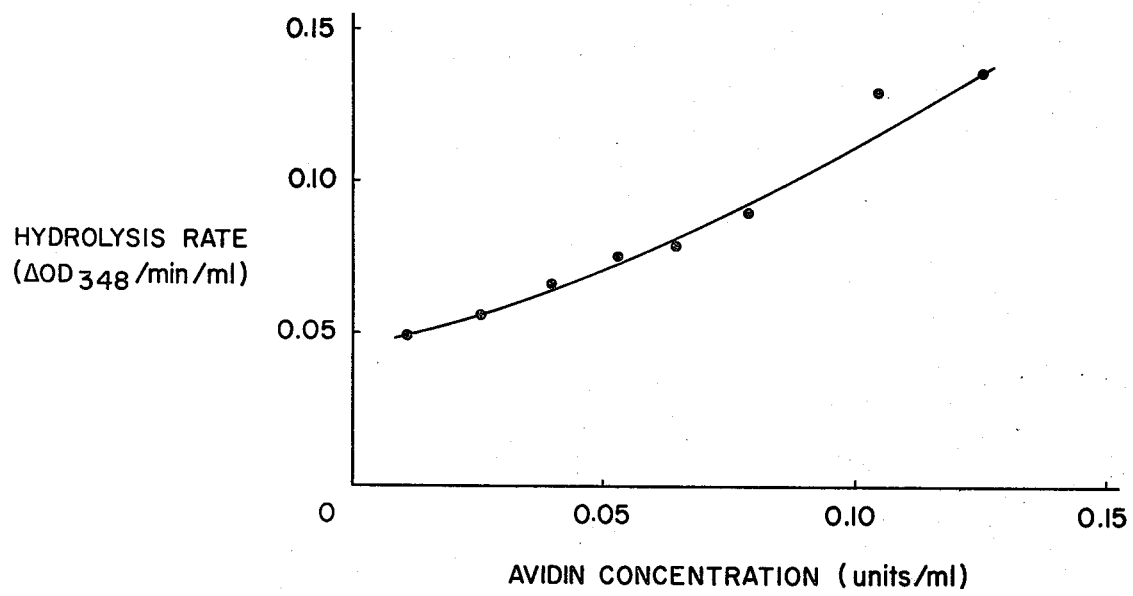
FIG. 2 is a graphic representation of the effect of various concentrations of avidin on the inhibitory effect of biotin-modulator conjugate on the esterase activity of carbonic anhydrase measured by hydrolysis rate.

The results, expressed as the average of duplicate measurements, are presented in Table 3. The results of reaction mixtures 2 through 9 are presented in graphical form in FIG. 2 of the drawing.

The results of reaction mixtures 2 through 9 demonstrate the effect of various levels of avidin on the inhibitory activity of biotin-modulator conjugate on esterase activities of carbonic anhydrase. For a constant level of biotin-modulator conjugate, the rate of enzymatic hydrolysis is directly related to the amount of avidin present. The results of reaction mixtures 8, 10, and 11 show that when biotin is present, the rate of hydrolysis is inversely related to the amount present.

Table 3

| Reaction Mixture | Biotin-Modulator Conjugate ($\mu$M) | Biotin ($\mu$M) | Auidin (units/ml) | Rate of Hydrolysis |
|---|---|---|---|---|
| 1 | — | — | — | 0.128 |
| 2 | 0.50 | — | 0.011 | 0.049 |
| 3 | 0.50 | — | 0.026 | 0.056 |
| 4 | 0.50 | — | 0.040 | 0.066 |
| 5 | 0.50 | — | 0.053 | 0.075 |

Table 3-continued

| Reaction Mixture | Biotin-Modulator Conjugate ($\mu$M) | Biotin ($\mu$M) | Auidin (units/ml) | Rate of Hydrolysis |
|---|---|---|---|---|
| 6 | 0.50 | — | 0.065 | 0.079 |
| 7 | 0.50 | — | 0.079 | 0.090 |
| 8 | 0.50 | — | 0.105 | 0.129 |
| 9 | 0.50 | — | 0.126 | 0.136 |
| 10 | 0.50 | 0.10 | 0.105 | 0.104 |
| 11 | 0.50 | 0.60 | 0.105 | 0.080 |

*Increase in Absorbance per min at 348 nm

EXAMPLE 5

Competitive Binding Assay for Dinitrophenyl (DNP) Derivatives; Use of Derivatized Acetazolamide as Labeling Substance A series of binding reaction mixtures were prepared, each to a volume of 0.66 ml and containing 100 $\mu$l 0.1M diethylmalonic buffer, pH 7.4, and the concentrations of acetazolamide, DNP-modulator (prepared as in Example 1, Part C), N-DNP-6 -aminocaproate [Biochem. J. 42:287(1948)], and antibody to DNP indicated in Table 4 (indicated concentrations based on 1 ml final volume). After a 5 min incubation at room temperature, 0.03 International Units carbonic anhydrase was added to each reaction mixture followed by an additional 5 min incubation. p-Nitrophenyl Acetate Reagent (0.33 ml) was then added and the rate of hydrolysis measured by monitoring absorbance at 348 nm.

The results, expressed as the average of duplicate measurements, are presented in Table 4. A comparison of the results of reaction mixtures 1, 3, and 5 shows that acetazolamide inhibited the carbonic anhydrase reaction and was substantially unaffected by the presence of antibody to DNP. Comparing the results of reaction mixtures 1, 2, and 4 reveals that the DNP-modulator conjugate also inhibited the carbonic anhydrase reaction, with the degree of inhibition being decreased by the presence of antibody to DNP. The result of reaction mixture 6 indicates that the presence of a DNP derivative had no substantial effect on the carbonic anhydrase reaction. A comparison of the results of reaction mixtures 2 and 7 shows that the presence of the DNP derivative could be determined by observing the increased inhibition of the carbonic anhydrase reaction by the DNP-modulator conjugate.

Table 4

| Reaction Mixture | Acetazolamide ($\mu$M) | DNP-Modulator Conjugate ($\mu$M) | N-DNP-6-amino caproate ($\mu$M) | Antibody to DNP ($\infty$l/ml) | Rate of Hydrolysis* |
|---|---|---|---|---|---|
| 1 | — | — | — | 100 | 0.153 |
| 2 | — | 0.278 | — | 100 | 0.108 |
| 3 | 0.216 | — | — | 100 | 0.091 |
| 4 | — | 0.278 | — | — | 0.074 |
| 5 | 0.216 | — | — | — | 0.088 |
| 6 | — | — | 1.8 | — | 0.154 |
| 7 | — | 0.278 | 1.8 | 100 | 0.098 |

*Increase in Absorbance per min at 348 nm

What is claimed is:

1. In a specific binding assay method for determining a ligand in a liquid medium,
    wherein said liquid medium is combined with reagent means including a conjugate of a labeling substance and a binding component to form a binding reaction system having a bound-species and a free-species of said conjugate; and
    wherein the amount of ligand present in said liquid medium is determined as a function of the amount of labeling substance present in said bound-species or said free-species;
    the improvement which comprises employing as said labeling substance a reversibly binding enzyme inhibitor, the binding constant for association of said inhibitor and an enzyme whose activity is inhibited thereby being less than about $10^{11}$ molar$^{-1}$; adding said enzyme whose activity is affected by said enzyme inhibitor to said bound-species or said free-species; and determining the amount of said enzyme inhibitor therein by measuring the resulting activity of said enzyme.

2. A method as claimed in claim 1 wherein the binding constant for the association of said reversibly binding enzyme inhibitor and said enzyme is between about $10^5$ and about $10^9$ molar$^{-1}$.

3. A method as claimed in claim 1 wherein said reversibly binding enzyme inhibitor is a competitive inhibitor of the enzyme.

4. A method as claimed in claim 3 wherein said reversibly binding competitive inhibitor and the enzyme inhibited thereby are, respectively,
    (a) acetazolamide, or an effective analog thereof, and carbonic anhydrase;
    (b) sulfanilamide, or an effective analog thereof, and carbonic anhydrase;
    (c) phenyl trimethylammonium ion, or an effective analog thereof, and acetylcholinesterase;
    (d) saccharo-1,4-lactone, or an effective analog thereof, and $\beta$-glucuronidase;
    (e) 4-amino-10-methyl-pteroylglutamic acid, or an effective analog thereof, and dihydrofolate reductase; or
    (f) 2,6,8-trichloropurine, or an effective analog thereof, and uricase.

5. A method as claimed in claim 1 wherein said enzyme inhibitor, as a component of said conjugate, affects the activity of said enzyme differently when said conjugate is in said bound-species than when in said free-species.

6. A method as claimed in claim 5 of the homogeneous type wherein said enzyme is added to the combined bound-species and free-species.

7. A method as claimed in claim 1 of the heterogenous type wherein said bound-species and said free-species are physically separated, and said enzyme is added to one thereof.

8. A method as claimed in claim 1 wherein said ligand is selected from the group consisting of antigens and antibodies thereto; haptens and antibodies thereto; and hormones, vitamins, metabolites, and pharmacological agents, and their receptors and binding substances.

9. In a reagent means for use in determining a ligand in a liquid medium, which means includes a conjugate of a labeling substance and a binding component, which means and the ligand form a binding reaction system having a bound-species and a free-species of said conjugate, the improvement wherein said labeling substance is a reversibly binding enzyme inhibitor and said means comprises additionally an enzyme whose activity is affected by said enzyme inhibitor, the binding constant for association of said inhibitor and said enzyme being less than about $10^{11}$ molar$^{-1}$.

10. Means as claimed in claim 9 wherein the binding constant for the association of said reversibly binding enzyme inhibitor and said enzyme is between about $10^5$ and about $10^9$ molar$^{-1}$.

11. Means as claimed in claim 9 wherein said reversibly binding enzyme inhibitor is a competitive inhibitor of the enzyme.

12. Means as claimed in claim 11 wherein said reversibly binding competitive inhibitor and the enzyme inhibited thereby are, respectively,
  (a) acetazolamide, or an effective analog thereof, and carbonic anhydrase;
  (b) sulfanilamide, or an effective analog thereof, and carbonic anhydrase;
  (c) phenyl trimethylammonium ion, or an effective analog thereof, and acetylcholinesterase;
  (d) saccharo-1,4-lactone, or an effective analog thereof, and β-glucuronidase;
  (e) 4-amino-10-methyl-pteroylglutamic acid, or an effective analog thereof, and dihydrofolate reductase; or
  (f) 2,6,8-trichloropurine, or an effective analog thereof, and uricase.

13. Means as claimed in claim 9 wherein said enzyme inhibitor, as a component of said conjugate, affects the activity of said enzyme differently when said conjugate is in said bound-species than when in said free-species, said means comprising (i) said conjugate wherein said binding component is said ligand, a specific binding analog of said ligand, or a specific binding partner of said ligand, and (ii) if said binding component is said ligand or a specific binding analog thereof, a specific binding partner of said ligand.

14. Means as in claim 9 which comprises (i) said conjugate wherein said binding component is said ligand or a specific binding analog of said ligand, and (ii) a specific binding partner of said ligand.

15. Means as in claim 14 wherein one of said conjugate and said specific binding partner is in a form which is insoluble in said liquid medium.

16. Means as in claim 9 which comprises (i) said conjugate in a form which is soluble in said liquid medium and wherein said binding component is a specific binding partner of said ligand, and (ii) said ligand or a specific binding analog thereof in a form which is insoluble in said liquid medium.

17. Means as in claim 9 which comprises (i) said conjugate wherein said binding component is a specific binding partner of said ligand, and (ii) a specific binding partner of said ligand.

18. Means as in claim 17 wherein one of said conjugate and said specific binding partner is in a form which is insoluble in said liquid medium.

19. Means as in claim 9 wherein said ligand is selected from the group consisting of antigens and antibodies thereto; haptens and antibodies thereto; and hormones, vitamins, metabolites, and pharmacological agents, and their receptors and binding substances.

* * * * *